United States Patent [19]

Shabel et al.

[11] Patent Number: 4,621,523
[45] Date of Patent: Nov. 11, 1986

[54] RAPID DETERMINATION OF METAL STRENGTH FROM HARDNESS TESTS

[75] Inventors: Barrie S. Shabel, Murrysville; Robert F. Young, Allegheny Township, Allegheny County, both of Pa.

[73] Assignee: Aluminum Company of America, Pittsburgh, Pa.

[21] Appl. No.: 746,321

[22] Filed: Jun. 19, 1985

Related U.S. Application Data

[63] Continuation-in-part of Ser. No. 544,735, Oct. 24, 1983, Pat. No. 4,530,235.

[51] Int. Cl.$^4$ .............................................. G01N 3/48
[52] U.S. Cl. ...................................................... 73/81
[58] Field of Search ......................... 73/81, 82, 83, 85

[56] References Cited

U.S. PATENT DOCUMENTS

| | | | |
|---|---|---|---|
| 3,969,928 | 7/1976 | Zarka | 73/81 |
| 4,147,052 | 4/1979 | Tsujiuchi et al. | 73/81 |
| 4,182,164 | 1/1980 | Fohey | 73/83 |
| 4,331,026 | 5/1982 | Howard et al. | 73/81 |
| 4,530,235 | 7/1985 | Shabel | 73/81 |
| 4,534,212 | 8/1985 | Targosz | 73/83 |

OTHER PUBLICATIONS

George, Estimating Yield Strength From Hardness Data, May 1976, pp. 30-35, Metal Progress.

Primary Examiner—Stewart J. Levy
Assistant Examiner—Robert R. Raevis
Attorney, Agent, or Firm—Elroy Strickland

[57] ABSTRACT

Means and method for making rapid determinations of the strength of metal materials from hardness evaluations of the materials. The means comprises an indentor for making impressions in a metal material, the indentor having a known predetermined dimension. Apparatus for mechanically directing the indentor against the material is provided and mechanically connected to the indentor. The driving apparatus moves the indentor against the material under successive predetermined loads or forces and in a manner that makes a series of impressions in the material. Means are provided for characterizing the respective geometries of the impressions, and means are provided for utilizing the dimension of the indentor, the values of the applied loads, and the respective geometries, to calculate the yield and/or tensile strength of the material therefrom.

3 Claims, 2 Drawing Figures

RAPID DETERMINATION OF METAL STRENGTH FROM HARDNESS TESTS

This application is a continuation-in-part of U.S. application Ser. No. 544,735 filed Oct. 24, 1983; now U.S. Pat. No. 4,530,235; issued July 23, 1985.

BACKGROUND OF THE INVENTION

The invention relates generally to an improvement in an apparatus and procedures for making rapid determination of the strength of metal materials from hardness evaluation of the materials, and particularly to the elimination of errors and uncertainties in conventional hardness testing techniques that relate yield and/or tensile strength to hardness.

Hardness evaluations are commonly employed in quality assurance testing to indicate material strength. Typically, correlations for particular alloy-temper combinations are expressed as equations relating strength (S) to an observed hardness number (H) in the form of $$S = a + b \times H \tag{1}$$

where the values of a and b depend on the hardness test scale selected, i.e., on the conditions of the hardness test.

Small scale tests, such as hardness tests, are convenient and less expensive than tests involving machined or otherwise specially prepared specimens for tensile testing. However, such convenience has led to a bewildering variety of hardness test scales. Generically, these can be divided into scales using ball-shaped indentors such as the Brinell and Rockwell indentors or diamond-shaped indentors such as Vickers or Knoop.

One significant disadvantage of the Rockwell test lies in the large variety of scales, i.e, no single scale adequately spans the whole range of interest for aluminum alloys, for example. Each scale has an optimal application in terms of material strength (temper) and minimum thickness necessary to avoid the so-called anvil effect, which effect involves variations in hardness readings due to the hardness of the structure supporting the specimen.

Nonetheless, for approximate practical purposes, the Rockwell scales can be ranked in terms of their severity of loading by dividing the applied measured pressure or load (L) by the diameter of the ball squared ($D^2$), which is the ratio $L/D^2$. If the reading on a particular scale is above say 100 (a hardness number), one has to then provide a scale with lower numerical readings; if the normal scale produces low readings, such as values below 20, a scale with a lower $L/D^2$ value is needed. This often necessitates changing scales in the midst of an investigation, which further complicates the use of a strength hardness equation such as equation (1) above.

Rockwell and other hardness tests, in addition, do not provide unambiguous predictions of yield or tensile strength of materials tested. This is the result of the influence of work hardening that occurs in the process of making the impressions. This influence can be understood by expressing hardness as a flow stress and relating it to yield or tensile strength through the well-known, constitutive stress-strain relationship.

The general conclusion from such analyses has been that one must know the work-hardening coefficient and the degree of strain imparted by the indentation process to predict yield or tensile strength from a hardness test.

An empirical way of circumventing the need for such complete knowledge was proposed in an article entitled "Estimating Yield Strength from Hardness Data" by Robert A. George, Subimal Dinda and Arthur S. Kasper, published in the May 1976 issue of *Metal Progress*. The authors use the basic relationship between applied force or load (L), indentor diameter (D) and the impression (d) of the form $$\frac{L}{d^2} = A\left(\frac{d}{D}\right)^m \tag{2}$$

to predict yield strengths of various steels. (A and m are empirical constants discussed in detail hereinafter.) This work correlated yield strength with the constant A in the form of a regression equation, i.e., $$\text{ys (ksi)} = 0.325A \tag{3}$$

with A being determined from a nomographic solution to equation (2) with particular Rockwell numbers. The A value, as determined by such a method, is the solution to equation (2) with d/D being equal to 1.0 (one); here A is only a single value that is employed to estimate the yield strength of the metal tested from an empirical relationship, i.e., equation (3). In this work, there is no indication of the tensile strength of the material.

In a paper entitled, "Flow Property Measurements from Instrumented Hardness Tests" by P. Au, G. E. Lucas, J. W. Sheckerd and G. R. Odette, published in 1980 by the American Society for Metals, a procedure similar to the above George et al paper correlates flow property information developed from instrumented hardness tests with true plastic strain of the samples tested.

However, the disclosure by Au et al requires certain assumptions concerning interfacial pressure (Pm) and axial flow of the specimen ($\sigma_t$), as discussed on pages 600 and 601 of the article and formulated by the equations $PM = 2.8\sigma_t$ and $$\epsilon p \approx .2\left(\frac{d}{D}\right).$$

The applicant's approach does not require these assumptions.

In addition, Au et al do not specifically show that hardness type measurements yield engineering tensile and/or yield strength estimates, as disclosed and taught by Applicant.

And lastly, it should be noted that the Au et al strain range is only about $0.01 < \epsilon p < 0.07$ (FIGS. 3–7 of the article), which corresponds to $$.05\left(\frac{d}{D}\right) < .35,$$

i.e., a much smaller range of hardness than that covered by Applicant's approach, as discussed below.

BRIEF SUMMARY OF THE INVENTION

The present invention takes into account the work hardening phenomenon that occurs in hardness evaluations that use mechanical indentors, thereby providing more precise estimates of both the yield and tensile strength from the results of such hardness evaluations. The invention uses the basic relationship of equation (2), the quantity $L/d^2$ in the equation is equal to $(\pi/4)$ times the "Meyer" hardness and is analogous to the stress which a specimen experiences in tensile testing.

The invention further uses the known empirical observations that the effective plastic strain ($\epsilon$) in the volume of metal being deformed by an indentor is related to the relaxed diametral ratio, $d/D^*$. Previous workers assumed $\epsilon$ (old)$=\alpha(d/D)$, where $0.2<\alpha<0.4$ but, because of elastic springback $D^*$ is greater than $D$ ($D^*>D$). By analogy to the case of total versus plastic tensile strain, we have related the unrecovered (plastic) strain to $d/D^*$ since d is essentially unchanged by springback. Thus we have the relationship $$\epsilon_{eff} = \alpha \left( \frac{d}{D^*} \right) \qquad (4)$$

This then yields a new, modified form of equation (2), namely, $$\frac{L}{d^2} = A \left( \frac{d}{D^*} \right)^m \qquad (5)$$

Since the Meyer hardness is analogous to stress, there is a similarity between equation (5) and the familiar power law equation $$\sigma = k\epsilon^n \qquad (6)$$

that represents the true stress ($\sigma$) and plastic strain ($\epsilon$) behavior of metal material in the range of uniform plastic elongation.

The quantity $D^*$ in equations (4) and (5) represents the effective or relaxed indentor diameter, defined as twice the impression radius of curvature calculated by allowing for the relaxation of the sample that occurs on removal of the applied load after the hardness test. A procedure to do this has been described in a previous publication (D. G. Rickerby, *Material Science and Engineering*, Vol. 56 (1982), p. 195) but was not applied by that author to the use developed here. Such an analysis is necessary for a correct description of the material behavior under our hardness test conditions.

Using these considerations, the present invention employs the concept of rapidly testing materials with different L and D combinations to determine A and m using equation (5). A low strain flow stress value of $L/d^2$, i.e., at $d/D$ less than 0.2 is calculated. Typically, this quantity is calculated at $d/D^*=0.1$ and designated as A', while A is the calculated value at $d/D^*=1$. The values of A and A' are then correlated respectively with tensile and yield strength of the material tested, the use of two or more load and diameter combinations providing two or more points to obtain an accurate slope for a proper stress-strain curve for the material.

DESCRIPTION OF THE DRAWINGS

The advantages and objectives of the invention will be best understood from consideration of the following detailed description and the accompanying drawings, FIG. 1 of which is a diagrammatic representation of a system for making hardness tests and for calculating material strength therefrom, while FIG. 2 of the drawings is a flow diagram of the processes of the system.

PREFERRED EMBODIMENT

Figure 1:
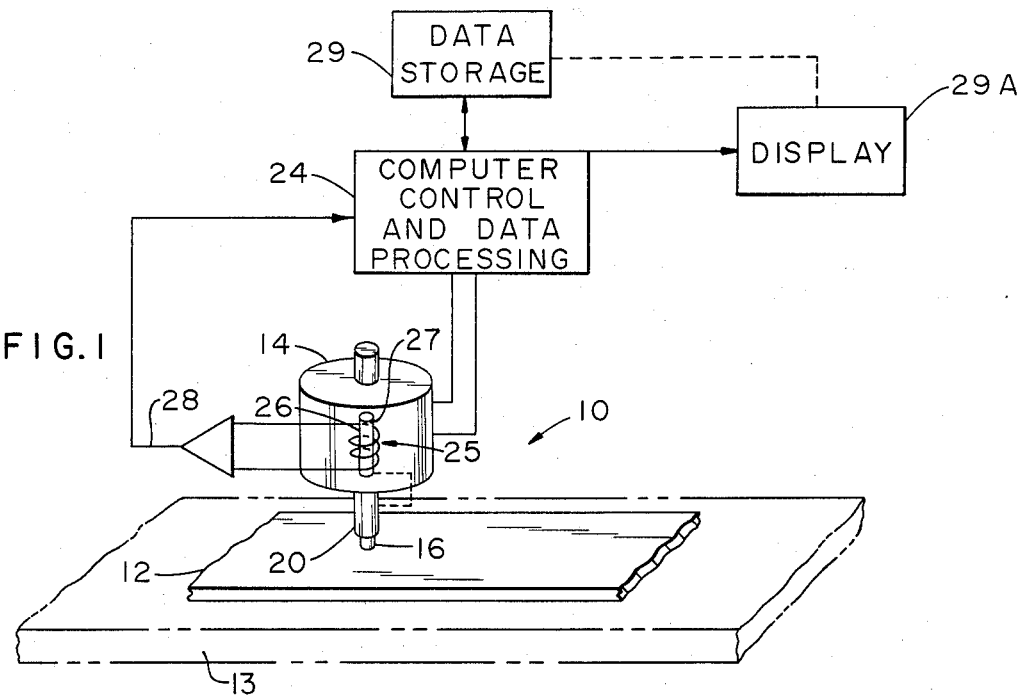

Referring now to the drawing, a system 10 is depicted schematically for rapidly providing impressions (not shown) in a metal workpiece 12, and for controlling and measuring the size (depth) of the impressions. Workpiece 12 is shown supported on a structure 13 that is rigid for purposes of making hardness tests involving the workpiece.

System 10 includes an actuator (cylinder) 14 adapted to translate an indentor 16 against workpiece 12 to form a series of impressions. The indentor is shown supported at the end of a probe and stem structure 20 extending from and mechanically connected to actuator 14.

The indentor shown in the drawing, and used in experiments that lead to the invention, is a ball or spherical structure such as may be employed in Rockwell scale hardness evaluations. Rockwell scale loads and penetrators were employed initially for their convenience only; the underlying methodology of the invention is not limited to any particular type of axisymmetric indentor and hardness measuring system.

The indentor can be applied to workpiece 12 by any suitable mechanism. One such mechanism is a double acting pneumatical cylinder (14), such as is shown in U.S. Pat. No. 4,331,026 to Howard et al. A cylinder allows continuous or discreet incremental movement of the indentor into the metal of the workpiece under a choice of loads (forces) at which the indentor is applied. The load applied by the indentor to the workpiece is a linear function of the pressures applied to the double acting cylinder. The value of the applied load may be predetermined by presetting the pressures to be applied to the cylinder or, alternatively, the load may be determined by measuring the pressures as they are applied. These functions can be controlled by a small computer 24 (a minicomputer or microprocessor) appropriately programmed and connected to actuator 14.

The indenting mechanism is also provided with means 25 to measure the depths of the impressions made in workpiece 12. These can be, for example, commercially available, linear voltage differential transformers (LVDTs) such as disclosed in U.S. Pat. No. 4,182,164 to Fohey. An LVDT has a stationary winding 26, an associated ferromagnetic core 27 that moves with the probe of indentor 16. The movement of the core changes the magnetic coupling between primary and secondary components of the stationary winding to provide an analogue DC output voltage at 28 indicative of the displacement of the core and hence the depth of penetration by the indentor. The diameter of each impression can be calculated, for example, by computer 24, from the impression depth and the diameter of the indentor, which is known.

Other means (not shown), such as optical devices, using light sources and detectors, can be employed to characterize the size of the impressions made in workpiece 12.

The operation of arrangement 10 is as follows. The workpiece 12 to be rapidly tested for its strength, which workpiece may be a metal plate or sheet product, an extrusion or forging, wire, rod or bar product, etc., is first placed on a rigid structure and surface 13 (which should conform to the shape of the product).

The diameter of the ball indentor and the loads or forces (i.e., the pressures to be applied to cylinder 14) under which the ball will be moved against the workpiece or product are chosen for the particular alloy and hardness of the product or workpiece. And, as discussed hereinafter, the system of the invention is suitable for establishing hardness to strength relationships for a variety of metal products, these relationships being employed for comparison to hardness readings obtained by the system when examining products for determination of their strengths.

With an appropriate ball diameter and two or more load values chosen for the particular material of the workpiece, the load values and ball diameter information are loaded into computer 24, and cylinder 14 ordered to drive indentor 16 against the exposed face of workpiece 12. The cylinder is now operated to direct indentor 16 against and into the upper surface of workpiece 12 under the force of the chosen loads; the indentor thereby forms a series of impressions in the workpiece.

The series of impressions can be formed by translating the workpiece or cylinder-indentor after each impression is made, or superposed impressions can be formed continuously by continuously applied pressure effected by cylinder 14. Similarly, superposed impressions can be formed by distinct, incremental increases in load applied by the cylinder. In all cases, the LVDT 25 measures the depths of the impressions and outputs signals at 28, representing such measured depths, to computer 24. The diameters of the impressions are then rapidly calculated by the computer using well-known geometric procedures, remembering that the diameter of the ball indentor is already known by the computer. This provides two or more force-diameter combinations that are employed to obtain an accurate slope for the stress-strain curve of the material of the workpiece.

Figure 2:
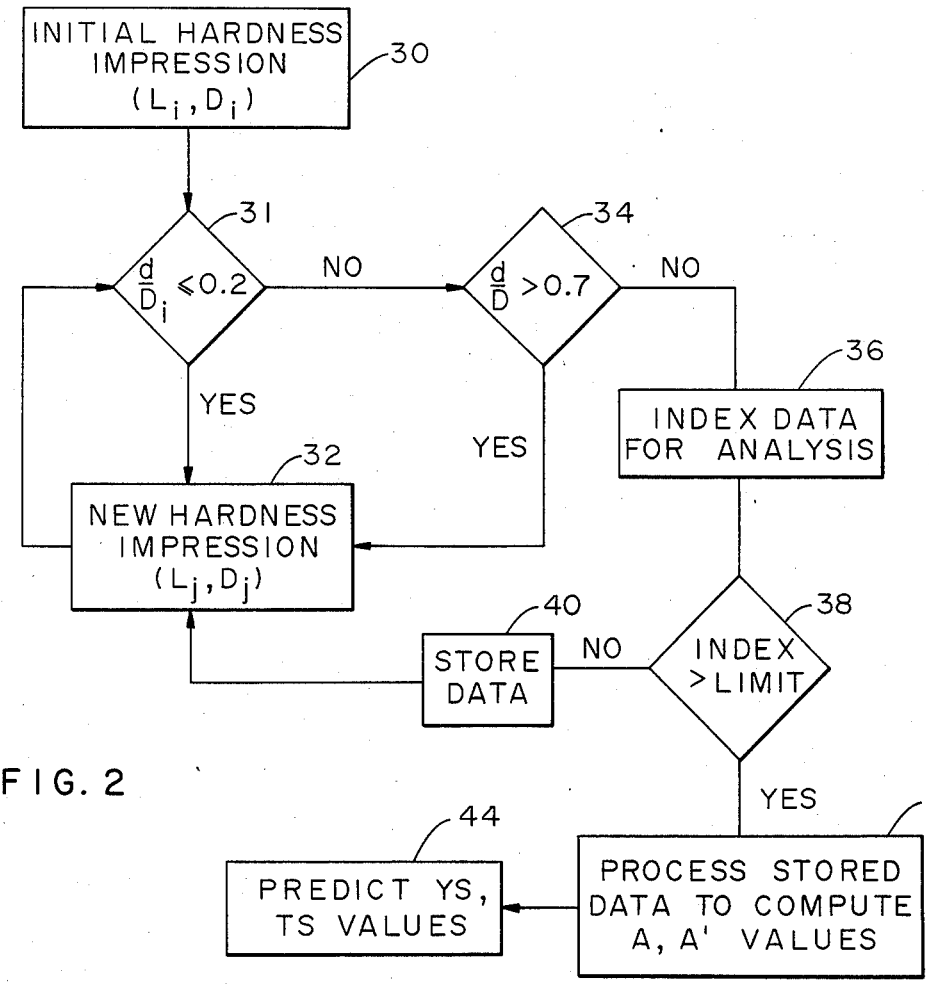

The process of the analysis of the invention as performed by computer 24 and a storage device 29 discussed in detail hereinafter is better explained by the flowchart of FIG. 2. More particularly, at location or box 30 in FIG. 2, a person operating the system 10 calls for an initial impression by indentor 16. If the impression diameter ratio (d/D) is characterized at 31 as being less than the minimum acceptable value, typically between 0.1 and 0.2, which is a "yes" answer for the logic of 31, the computer calls for another deeper impression at 32 using a greater load (via cylinder 22) applied to the indentor or a smaller indentor 16 with the same load. This step is repeated until an indentation of sufficient depth is made and a "no" answer is forthcoming from 31.

With the "no" answer from 31, the computer now tests at 34 whether the indentation or impression ratio d/D is greater than some upper limit, say 0.7. If the answer from 34 is "yes," another impression is again made at 32 using conditions that will result in d/D being less than the upper limit, (but greater than the minimum value noted above, e.g., 0.2). When this occurs, a "no" answer is produced at 34.

Available to computer 24 and to operating personnel via a display device 29A are now at least two distinct indications of the hardness of the product, i.e., at least two combinations of L and d at which the indentor moved into the material of 12.

With a "no" answer from decision 34 the number of data points of impression characterizations, i.e., of load values to diameter ratios ($L/d^2$) denoting hardness of the workpiece is indexed at 36 for future analysis. However, if the number of points now available is not considered adequate (at 38) to provide good analysis and accurate prediction of the yield and tensile strength of the workpiece under test, the decision is made at 38 to store (at 40), in storage device 29 of FIG. 1, the data of the points that have been made, and to order (again at 32) additional impressions in the workpiece until a sufficient number of hardness points are available.

With a sufficient number of hardness (data) points, i.e., with a "yes" at 38, the computer processes at 42 certain data that is stored in 29 (FIG. 1) to provide predictions at 44 of the tensile and yield strength of the workpiece. This is accomplished in the following manner.

As indicated above, the parameter $L/d^2$ is analogous to the stress, and above equation (2) indicates a similarity to the well-known stress versus strain relationship involved in tensile testing of metal specimens [equation (6)] when strain is expressed mathematically by the above equation (4).

The similarity between above equation (5) and the power law representing the true stress to strain relationship in tensile analysis indicates that the work-hardening capability of the material under test can also be estimated from equation (5). This is typically done with standard linear regression techniques where m is simply the slope of the logarithmic regression relating the $L/d^2$ and $d/D^*$ values. As a consequence, the low strain value correlates with yield strength while the high value correlates with tensile strength. For practical purposes, in experiments employing the principles of the subject invention, as explained hereinafter, it appears that a lower limit on $d/D^*$ is about 0.1.

The selectable loads and/or indentors employed in the process and system of the present invention provide the different L and D combinations to determine the A and m values via equation (2). The "low strain" flow stress, e.g., at $d/D = 0.1$, is calculated by the computer and is designated A'. The high strain value (A) is calculated using the equation and corresponds to the value of $L/d^2$ at $d/D$ equal to 1.

The results of these determinations are then compared to relationships that have been previously established between tensile strength and value A, and between yield strength and value A', via prior tests involving hardness and tensile evaluations. The results of these prior tests are stored in memory means 29 connected to computer 24. Computer 24 can then compare the readout of 25 with the results in 29 to correlate the tensile and/or yield strength determined from its calculations involving the impression geometry with the data stored in 29 (involving the prior established relationships of strength and hardness). For this process the computer uses established formulations, e.g.:

$$TS = K_1 A + K_2 \qquad (7a)$$

$$YS = K_3 A' + K_4 \qquad (7b)$$

where the numerical values of $K_1$ to $K_4$ depend on the stress units in which the TS or YS are to be expressed ($K_2$ and $K_4$ can also be equal to zero).

The system of the invention, in addition, can be used to provide the data for storage in 29. By using the impression geometry provided by 25 and at least two successive impressions in the material under test and fitting the same to equations (5) and (7), the strength to hardness relationship obtained thereby can be loaded into 29 for future correlation purposes.

The system of the present invention is employable as a control tool to conveniently monitor such processes as annealing, heat treating and artificial aging of metal products, as well as such mechanical processes as metal rolling and forming. This is particularly important in processes that directly affect the strength of the product produced.

What is claimed is:

1. Apparatus for making rapid determinations of yield and tensile strength of a metal workpiece from hardness evaluations of the workpiece, the apparatus comprising:
   at least one indentor for making impressions in metal workpieces, said indentor having a known predetermined dimension,
   means for directing the indentor against a metal workpiece at different known forces, the different forces being effective to form a series of impressions in the workpiece of different sizes,
   means for characterizing the geometries of the impressions, and
   means for utilizing the known forces, the known dimension of the indentor and the geometries of the impressions to calculate the yield and tensile strength of the workpiece.

2. The apparatus of claim 1 in which the means employed to calculate yield and tensile strength includes a computer capable of estimating A and m from hardness data using the equation $$\frac{L}{d^2} = A \left(\frac{d}{D^*}\right)^m$$

where
   L is each of the known forces at which the indentor is directed against the metal workpiece,
   d is the diameter of each of the impressions,
   D* is the relaxed diameter of the indentor, i.e., twice the radius of curvature of the impressions,
   A is a constant that is representative of the resistance of the metal of the workpiece that limits penetration by a spherical indentor, and
   m is a measure of the work hardening characteristic of the metal of the workpiece.

3. The apparatus of claim 2 in which the computer includes means for storing hardness data and for relating the same to the tensile and yield strength of a workpiece by utilization of relationships such as:

$$TS = K_1 A + K_2$$

$$YS = K_3 A' + K_4$$

where $K_1$ to $K_4$ are numerical values representing the stress units in which tensile strength (TS) and yield strength (YS) are to be expressed and A and A' are high and low strain flow stresses, respectively.

* * * * *